(12) United States Patent
Mazuir et al.

(10) Patent No.: US 12,019,027 B1
(45) Date of Patent: Jun. 25, 2024

(54) SYSTEMS AND ACCESSORIES FOR OPTICAL ANALYSIS OF SAMPLES ON PORTABLE ELECTRONIC DEVICES

(71) Applicant: Apple Inc., Cupertino, CA (US)

(72) Inventors: Clarisse Mazuir, San Jose, CA (US); Jack E. Graves, Sunnyvale, CA (US); Malcolm J. Northcott, Santa Cruz, CA (US)

(73) Assignee: Apple Inc., Cupertino, CA (US)

( * ) Notice: Subject to any disclaimer, the term of this patent is extended or adjusted under 35 U.S.C. 154(b) by 344 days.

(21) Appl. No.: 17/356,352

(22) Filed: Jun. 23, 2021

Related U.S. Application Data

(60) Provisional application No. 63/058,159, filed on Jul. 29, 2020.

(51) Int. Cl.
*G01N 21/78* (2006.01)
*G01N 21/77* (2006.01)
(Continued)

(52) U.S. Cl.
CPC ............ *G01N 21/78* (2013.01); *G03B 15/02* (2013.01); *G01N 2021/7769* (2013.01);
(Continued)

(58) Field of Classification Search
CPC ............ G01N 33/553; G01N 27/3272; G01N 27/3273; G01N 33/5308; G01N 33/54388; G01N 2021/7759; G01N 21/255; G01N 2201/062; G01N 2201/0221; G01N 21/532; G01N 21/51; G01N 2021/4726;
(Continued)

(56) References Cited

U.S. PATENT DOCUMENTS 9,185,200 B2 11/2015 Cunningham
9,244,066 B2 1/2016 O'Driscoll et al.
(Continued)

OTHER PUBLICATIONS

Zhu, Hongying, et al. "Optofluidic fluorescent imaging cytometry on a cell phone." Analytical chemistry 83.17 (2011): 6641-6647 (Year: 2011).*

(Continued)

*Primary Examiner* — Tarifur R Chowdhury
*Assistant Examiner* — Roberto Fabian, Jr.
(74) *Attorney, Agent, or Firm* — Treyz Law Group, P.C.; G. Victor Treyz; Kendall P. Woodruff

(57) ABSTRACT

A test system may be used to measure biological samples and other samples. Samples may be placed on a test substrate such as a test slide or other transparent substrate. The substrate may have patches of reactant-coated gold nanorods or other nanostructures that exhibit plasmonic resonances. An accessory may be removably coupled to a portable electronic device such as a cellular telephone. The accessory may have a lens and a light source that emits light into an edge of the test slide. The light may scatter from the nanostructures in a perpendicular direction towards a camera in the portable electronic device so that the portable electronic device can gather images of the illuminated substrate and measure spectral shifts associated with reactions between the samples and the reactant, thereby helping to analyze the composition of the samples.

18 Claims, 10 Drawing Sheets

(51) Int. Cl.
*G01N 33/543* (2006.01)
*G03B 15/02* (2021.01)
*H04M 1/02* (2006.01)

(52) U.S. Cl.
CPC ............... *G01N 2021/7796* (2013.01); *G01N 33/54386* (2013.01); *G01N 2800/26* (2013.01); *H04M 1/0264* (2013.01)

(58) Field of Classification Search
CPC .. G01N 33/48785; G16H 10/40; G16H 10/65; A61B 10/007
See application file for complete search history.

(56) References Cited

U.S. PATENT DOCUMENTS

| | | | | |
|---|---|---|---|---|
| 9,310,300 | B2* | 4/2016 | Alt | .......................... G01N 21/63 |
| 9,787,815 | B2 | 10/2017 | Erickson et al. | |
| 10,365,214 | B2* | 7/2019 | Ozcan | .................. G06T 7/0012 |
| 2012/0062882 | A1* | 3/2012 | Sakagami | ............ G01N 21/658 |
| | | | | 359/327 |
| 2014/0072189 | A1* | 3/2014 | Jena | .................... G01N 21/8483 |
| | | | | 382/128 |
| 2015/0253321 | A1* | 9/2015 | Chou | ................ G01N 33/54386 |
| | | | | 435/7.1 |
| 2016/0334614 | A1* | 11/2016 | Ozcan | .................. G02B 21/361 |
| 2017/0343480 | A1* | 11/2017 | Kwak | .............. G01N 33/48785 |

OTHER PUBLICATIONS

Cetin, Arif E., et al. "Handheld high-throughput plasmonic biosensor using computational on-chip imaging." Light: Science & Applications 3.1 (2014): e122-e122 (Year: 2014).*

Marinakos, Stella M., Sihai Chen, and Ashutosh Chilkoti. "Plasmonic detection of a model analyte in serum by a gold nanorod sensor." Analytical chemistry 79.14 (2007): 5278-5283 (Year: 2007).*

Gallegos et al., Label-free biodetection using a smartphone, Lab Chip, Apr. 3, 2013, pp. 2124-2132, Issue 13, RSC Publishing.

* cited by examiner

SYSTEMS AND ACCESSORIES FOR OPTICAL ANALYSIS OF SAMPLES ON PORTABLE ELECTRONIC DEVICES

This application claims the benefit of provisional patent application No. 63/058,159, filed Jul. 29, 2020, which is hereby incorporated by reference herein in its entirety.

FIELD

This relates generally to electronic device systems, and, more particularly, to electronic device systems for analyzing biological samples and other samples.

BACKGROUND

It may sometimes be desired to analyze samples. For example, it may be desirable to analyze biological samples using electronic equipment.

SUMMARY

A test system may be used to measure samples. In some scenarios, the samples being measured may be biological samples.

A sample may be placed on a test substrate such as a test slide or other transparent substrate. The substrate may have patches of reactant-coated gold nanorods or other nanostructures that exhibit plasmonic resonances when illuminated by light.

An accessory may be removably coupled to a portable electronic device such as a cellular telephone. The accessory may have a lens that is aligned with a rear-facing camera in the cellular telephone or other light sensor.

The accessory may also have a light source that emits light into an edge of the test slide. The light passes through the transparent test slide to the patches of reactant-coated nanorods or other nanostructures and scatters from the nanostructures in a perpendicular direction through the lens towards the camera.

The portable device can measure spectral shifts associated with reactions between viruses and other substances in samples and reactant on the nanostructures. These spectral shifts can be analyzed to help determine the composition of the samples (e.g., whether a sample contains a virus that binds with an antibody or other reactant).

DETAILED DESCRIPTION

Optical sensing techniques in which samples on transparent substrates are illuminated may be used to analyze surface defects, may be used to analyze surface contamination, may be used to analyze biological specimens, and/or may be used for testing other types of samples. Illustrative configurations in which biological samples are tested may sometimes be described herein as an example.

Figure 1:
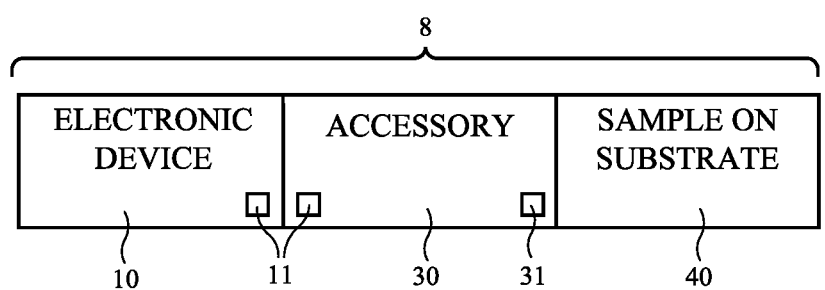
FIG. 1 is a schematic diagram of an illustrative system for analyzing samples in accordance with an embodiment.

An illustrative system for using optical testing techniques to analyze biological samples is shown in FIG. 1. System 8 may include an electronic device such as electronic device 10. Electronic device 10 of FIG. 1 may be a computing device such as a laptop computer, a tablet computer, a cellular telephone, a wristwatch, other portable electronic devices, or other electronic equipment. Configurations in which device 10 is a portable electronic device such as a cellular telephone may sometimes be described herein as an example.

Accessory 30 may be removably coupled to electronic device 10. If desired, attachment structures 11 (e.g., magnets for attracting device 10 to accessory 30 and vice versa, mating engagement structures such as clips, fasteners such as screws or hook-and-loop fasteners, adhesive, press-fit connections, mating protrusions and recesses, and/or other attachments structures) may be used in holding accessory 30 on device 10. Accessory 30 may be configured to receive a test slide or other transparent substrate 40 with a sample. Accessory 30 may have components such as a light source for illuminating the sample. If desired, accessory 30 may include a sensor such as sensor 31 (e.g., a switch, an optical sensor, or other sensor) that detects the presence of substrate 40 (e.g., so that illumination can be automatically provided in response to detecting substrate 40 in accessory 30).

During operation of system 8, the light source in accessory 30 may illuminate the sample on the transparent substrate while a camera or other light-sensitive component in electronic device 10 measures the illuminated sample. Reagent on the substrate may react or may not react with substances in the sample, depending on the nature of the sample. By analyzing the optical properties of the illuminated sample, it can be determined whether the sample has reacted with the reagent, thereby providing information on whether substances of interest are present in the sample.

Figure 2:
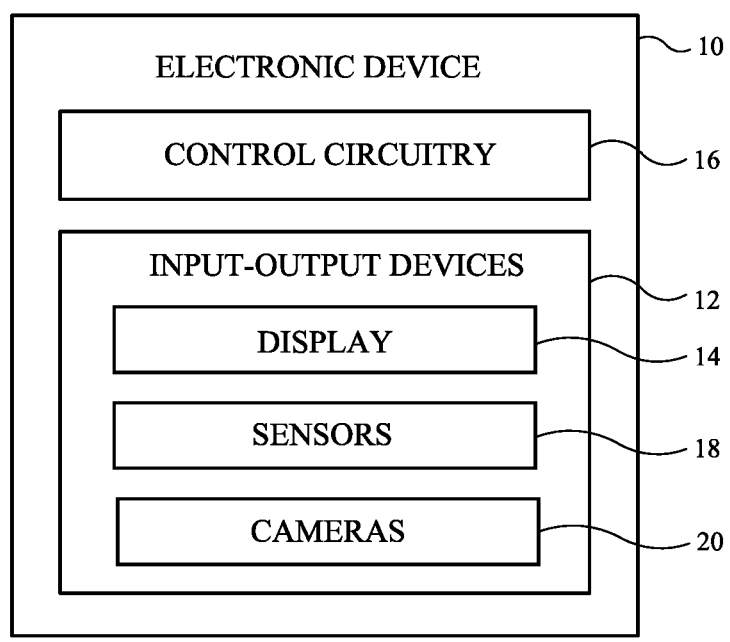
FIG. 2 is a schematic diagram of an illustrative electronic device in accordance with an embodiment.

FIG. 2 is a schematic diagram of an illustrative electronic device that may be used in system 8. As shown in FIG. 2, electronic device 10 may have control circuitry 16. Control circuitry 16 may include storage and processing circuitry for supporting the operation of device 10. The storage and processing circuitry may include storage such as hard disk drive storage, nonvolatile memory (e.g., flash memory or other electrically-programmable-read-only memory configured to form a solid state drive), volatile memory (e.g., static or dynamic random-access-memory), etc. Processing circuitry in control circuitry 16 may be used to control the operation of device 10. The processing circuitry may be based on one or more microprocessors, microcontrollers, digital signal processors, baseband processors, power management units, audio chips, application specific integrated circuits, etc. Control circuitry 16 may include communications circuitry for supporting wired and/or wireless communications between device 10 and external equipment. For example, control circuitry 16 may include wireless communications circuitry such as cellular telephone communications circuitry and wireless local area network communications circuitry. During operation, this communications circuitry may be used to communicate with corresponding communications circuitry in other devices (e.g., accessory 30, a remote server or other equipment for gathering test results, etc.).

Input-output circuitry in device 10 such as input-output devices 12 may be used to allow data to be supplied to device 10 and to allow data to be provided from device 10 to external devices. Input-output devices 12 may include buttons, joysticks, scrolling wheels, touch pads, key pads, keyboards, microphones, speakers, tone generators, vibrators, cameras, light-emitting diodes and other status indicators, data ports, etc. A user can control the operation of device 10 by supplying commands through input-output devices 12 and may receive status information and other output from device 10 using the output resources of input-output devices 12.

Input-output devices 12 may include one or more displays such as display 14. Display 14 may be a touch screen display that includes a touch sensor for gathering touch input from a user or display 14 may be insensitive to touch. A touch sensor for display 14 may be based on an array of capacitive touch sensor electrodes, acoustic touch sensor structures, resistive touch components, force-based touch sensor structures, a light-based touch sensor, or other suitable touch sensor arrangements.

Input-output devices 12 may also include sensors 18. Sensors 18 may include a capacitive sensor, a light-based proximity sensor, a magnetic sensor, an accelerometer, a force sensor, a touch sensor, a temperature sensor, a pressure sensor, a compass, a microphone, a radio-frequency sensor, a three-dimensional image sensor, an ambient light sensor, a light-based position sensor (e.g., a lidar sensor), and other sensors. Input-output devices may also include one or more cameras 20 (e.g., two dimensional cameras). Cameras 20 may include color digital image sensors for capturing images. Cameras 20 and/or other optical sensors (e.g., a color ambient light sensor, etc.) may also be used to analyze light from illuminated test samples. Configurations in which a rear facing camera is used in measuring samples may sometimes be described herein as an example.

Figure 3:
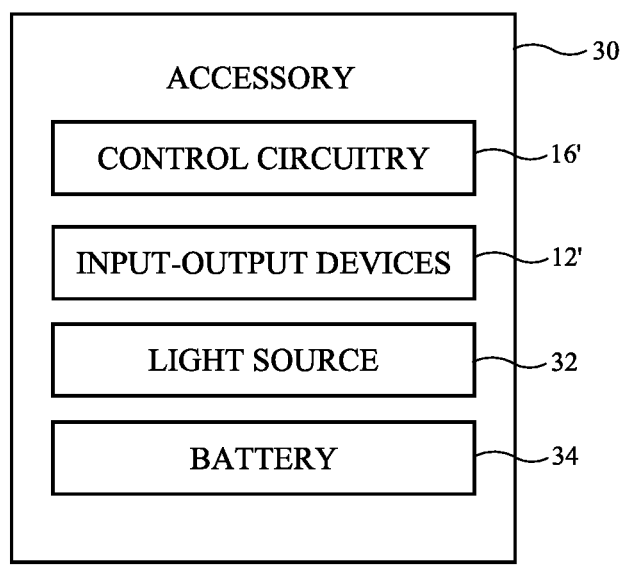
FIG. 3 is a schematic diagram of an illustrative electronic device accessory such as a sample illuminator in accordance with an embodiment.

A schematic diagram of an illustrative accessory that may be used in system 8 to make sample measurements is shown in FIG. 3. As shown in FIG. 3, accessory 30 may include control circuitry 16' (e.g., control circuitry such as circuitry 16 of FIG. 2) and input-output devices 12' (e.g., input-output devices such as input-output devices 12 of FIG. 2). Accessory 30 may have a wired connection to a source of power (e.g., a wired connection to device 10 or a separate power source), may have a wireless power receiving circuit for receiving wireless power from a wireless power transmitter in device 10 or other wireless power transmitting circuitry, and/or may have a local source of power such as battery 34 (e.g., a removable battery and/or a rechargeable battery).

Light source 32 may be used to illuminate a sample on a transparent sample substrate (e.g., substrate 40 of FIG. 1) during operation of system 8. Light source 32 may include light-emitting diodes, lasers, other semiconductor light-emitting devices, and/or other sources of light. Illumination may be provided at visible wavelengths and/or other wavelengths. In an illustrative configuration, multiple light-emitting devices (e.g., diodes and/or lasers) are included in light source 32 and these devices include devices that emit light at multiple wavelengths (e.g., a first wavelength, a second wavelength, and, if desired, additional wavelengths). White light illumination sources, infrared illumination sources, ultraviolet illumination sources, and/or other light sources may be included in light source 32, if desired.

Figure 4:
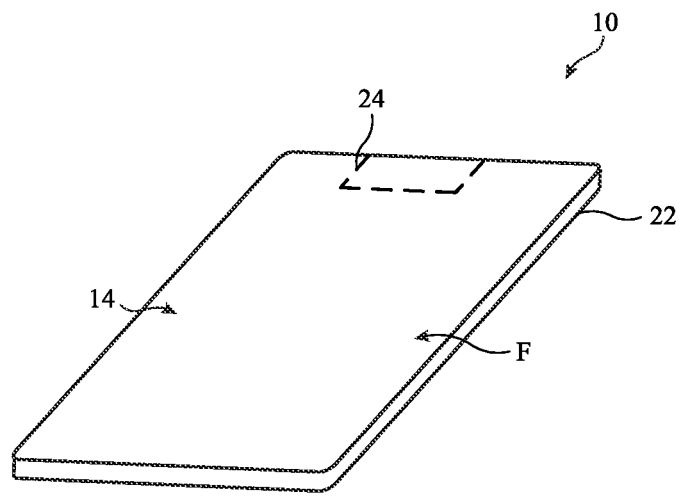
FIG. 4 is a front perspective view of an illustrative electronic device in accordance with an embodiment.
Figure 5:
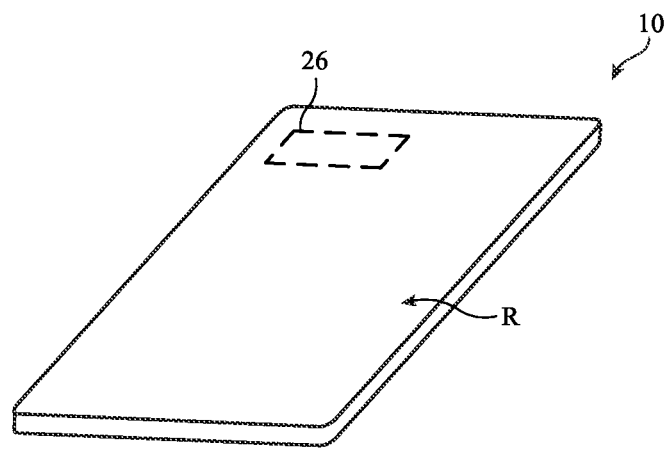
FIG. 5 is a rear perspective view of an illustrative electronic device in accordance with an embodiment.

FIGS. 4 and 5 are perspective views of an illustrative electronic device for use in system 8. Device 10 of FIGS. 4 and 5 may be, as an example, a portable electronic device such as a cellular telephone or tablet computer (as examples).

FIG. 4 is a front perspective view of device 10 showing how display 14 may be mounted on front face F of device 10. Housing 22 may separate an interior region in device 10 that includes control circuitry 16 and input-output devices 12 (FIG. 1) from an exterior region surrounding device 10. Housing 22 may be formed from metal, polymer, glass, ceramic, other materials, and/or combinations of these materials.

Components may be mounted in region 24 or other suitable portion of front face F. These components may include an ambient light sensor, a proximity sensor, a three-dimensional infrared image sensor, light sources, a speaker, a microphone, and other electronic components. The components in region 24 may also include a front-facing camera.

FIG. 5 is a rear perspective view of device 10. Housing 22 may cover rear face R of device 10. Rear face R may have a region such as region 26 in which one or more components such as one or more camera flashes (light-emitting diodes) and one or more rear-facing cameras may be mounted. Each rear-facing camera may include a lens and a corresponding digital image sensor for capturing images through the lens. The digital image sensor may include pixels of different colors such as red, green, and blue pixels, thereby allowing the camera to make light intensity measurements at multiple wavelength bands (e.g., a red wavelength band, a blue wavelength band, and a green wavelength band).

During sample measurements with system 8, accessory 30 may illuminate a sample on substrate 40 using light source 32. Substrate 40 may include reagent configured to react with one or more substances in samples. The reagent may, as an example, include antibodies (e.g., antibodies configured to react with a specific virus, one or more proteins (e.g., protein configured to react in the presence of saliva), and/or other reagents. The reagents may be provided as coatings on nanostructures. The nanostructures may, as an example, be gold nanorods, nanorods or other metallic nanoparticles formed from one or more other metals, or other nanoparticles that exhibit plasmon resonance when illuminated by light. By monitoring changes in the plasmon resonance behavior of the nanostructures with a rear-facing camera in region 26 of device 10 (FIG. 5) or other sensor in device 10, information can be gathered on a sample under test.

Figure 6:
FIG. 6 is a top view of an illustrative sample substrate formed from a transparent member such as a glass slide in accordance with an embodiment.

FIG. 6 is a top view of an illustrative transparent substrate. Substrate 40 of FIG. 6 includes test patches 42. There are four test patches 42 in the example of FIG. 6. Fewer test patches (e.g., a single test patch, two test patches, or three test patches) or more test patches (e.g., at least five test patches) may be used, if desired. Test patches 42 may include one or more patches with nanostructures (e.g., gold nanorods or nanorods or other nanostructures formed from other elemental metals, metal alloys, or other nanoparticles) that are uncoated with reagent and that therefore serve as a control. Test patches 42 may also contain one or more patches coated with reagent (e.g., antibodies, saliva-reacting protein, etc.). A test patch coated with saliva-reacting protein may be used to ensure that saliva from a sample is present on substrate 40 (e.g., to confirm that a valid sample is actually on place on substrate 40 before tests results are generated). A test patch with antibodies may be used to detect whether a particular virus is present in a sample. A test patch that serves as a control (e.g., a patch with uncoated nanostructures) may be used to produce a reference signal that can be compared with signals from patches with reagent that react with samples.

Patches 42 may have any suitable size and shape. For example, patches 42 may be circular, oval, rectangular, strip-shaped, square, etc. Patches 42 may be organized in an array having rows and columns, may be arranged in a line, and/or may have other suitable layouts. In an illustrative configuration, patches 42 are circular and have a diameter of 25-75 microns. Other patch configurations may be used, if desired.

Figure 7:
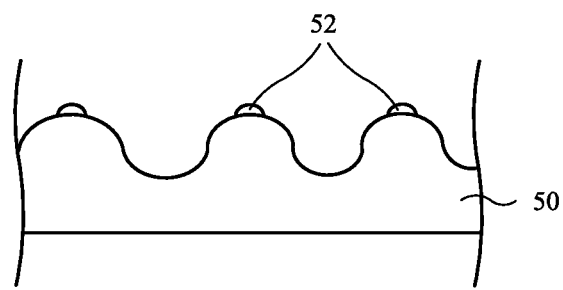
FIG. 7 is a cross-sectional side view of a layer with nanostructures in accordance with an embodiment.
Figure 8:
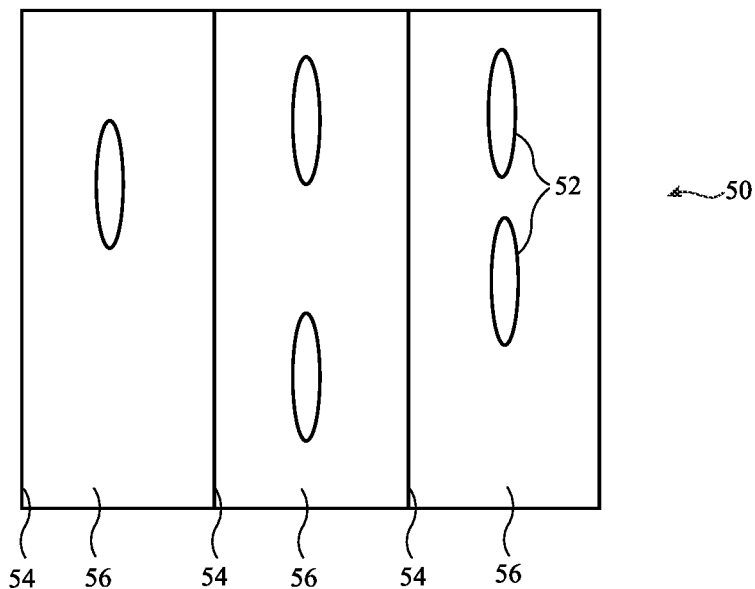
FIG. 8 is a top view of a layer with longitudinally aligned nanostructures in accordance with an embodiment.

Nanorods and other nanostructures may be formed using any suitable fabrication process. As an example, a corrugated surface (e.g. a corrugated polymer layer) may be created as shown by corrugated polymer layer 50 of FIG. 7. A blanket layer (e.g., a thin-film gold layer) may be deposited on the surface of layer 50 and etched to remove all but rod-shaped regions of the blanket layer (see, e.g., nanostructures 52 of FIG. 7, which may extend into the page of FIG. 7). If desired, nanorods or other nanostructures may be formed by annealing blanket metal films and causing the annealed metal to separate into individual nanostructures, by nanoimprinting, by electron beam lithography, and/or by other fabrication techniques. If desired, nanorods or other nanostructures for patches 42 may be oriented along preferred directions. For example, nanorods may be coated on a corrugated surface. The presence of the corrugations of this surface may help align the longitudinal axes of the nanorods with an axis that runs parallel to the corrugations as shown in the top view of FIG. 8 in which nanostructures 52 have been formed on corrugated surface such as layer 50 with longitudinally extending ridges 54 and grooves 56. This type of arrangement may be used to help align the electric field of at least some of the illuminating light with the longitudinal nanorod axes. Arrangements in which nanostructures are not aligned with the electric field of illuminating light and/or in which nanostructures are oriented randomly within test patches 42 may be used, if desired.

Figure 9:
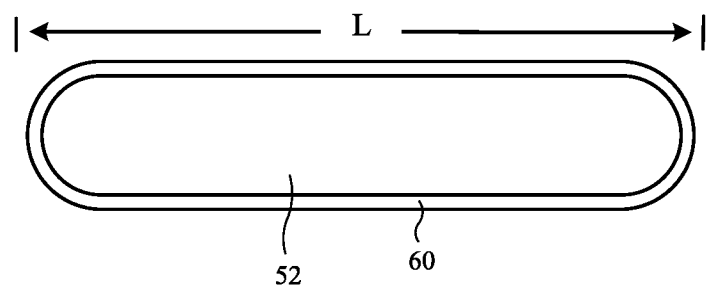
FIG. 9 is a cross-sectional side view of an illustrative nanostructure coated with reagent in accordance with an embodiment.
Figure 10:
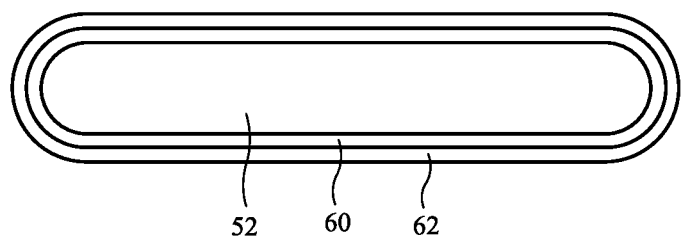
FIG. 10 is a cross-sectional side view of an illustrative nanostructure coated with reagent that has reacted with a sample in accordance with an embodiment.

FIGS. 9 and 10 are cross-sectional side views of nanostructures on substrate 40 (e.g., nanostructures that may be used to form test patches 42) before and after exposure to a sample (e.g., saliva or other body fluid, etc.). As shown in the cross-sectional side view of FIG. 9, nanostructures 52 may be characterized by nanoscale sizes (e.g., a length L of at least 5 nm, at least 10 nm, at least 20 nm, at least 40 nm, at least 80 nm, at least 160 nm, at least 320 nm, less than 400 nm, less than 200 nm, less than 100 nm, or other suitable length and a width that is equal to the length or that is less than the length to form an elongated nanorod). Initially, nanostructures 52 in patches 42 may be coated with reagent 60. The reagent coating may be an antibody, a protein, or other reagent. As an example, the reagent may be antibody that is known to bind to a virus of interest or may be a protein that reacts with the components in human saliva (e.g., to confirm when patches 42 on substrate 40 have been exposed to saliva). When exposed to a body fluid (e.g., saliva, blood, etc.), viruses, proteins, and other substances in the body fluid may or may not react with the reactant. In the absence of attraction between the body fluid substances and reagent 60, nanostructures 52 may retain an appearance of the type shown in FIG. 9 in which reagent 60 is uncoated with additional substances.

If a substance in the sample such as a component of saliva, a virus, or other substance reacts with and binds to reagent 60, nanostructures 52 will become coated with a layer of the material that has reacted with and bound to the reagent. As shown in FIG. 10, for example, sample coating 62 (e.g., a substance such as a component of saliva, a virus of interest, etc.) may bind to and form a coating layer on reagent 60. The presence of coating 62 (e.g., a dielectric of a particular thickness and dielectric constant) affects the plasmon resonance of nanostructures 52 when exposed to illumination and can be measured by device 10. To create a control (e.g., nanostructures that are expected not to respond to the presence of a sample), one or more of patches 42 may include uncoated nanostructures (e.g., nanostructures that are not coated with reagent). By measuring the light scattered from one or more sets of nanostructures (e.g. uncoated nanostructures, nanostructures coated with a first reagent such as a saliva-detecting protein, nanostructures coated with a second reagent such as a virus-detecting antibody, etc.), device 10 can analyze the sample of substrate 40.

Figure 11:
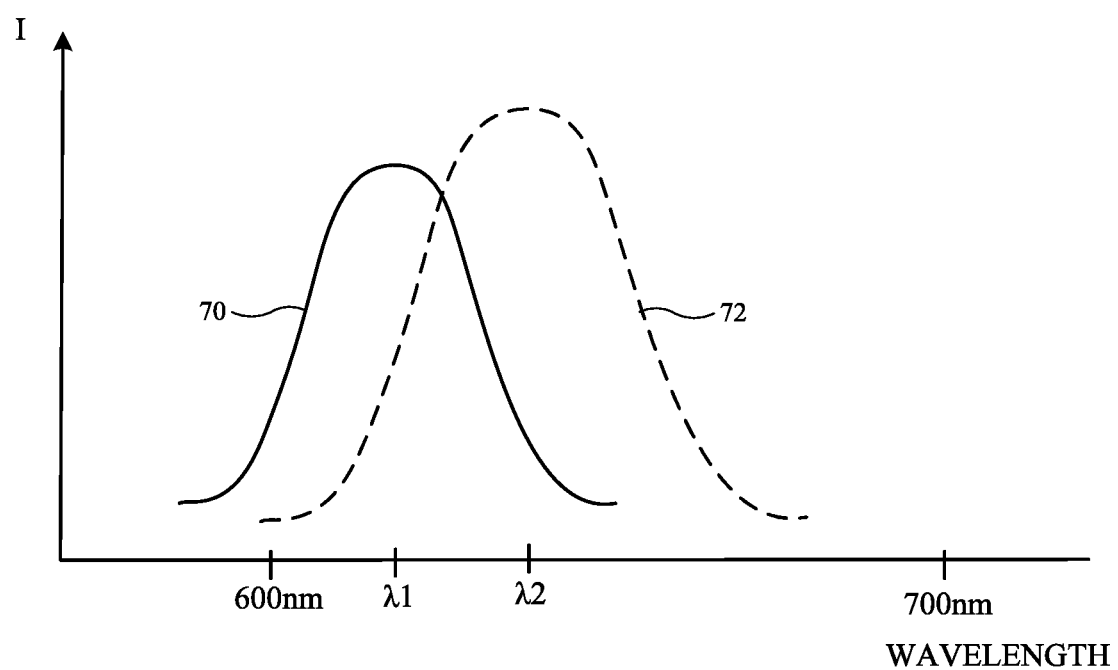
FIG. 11 is a graph of output light intensity versus illumination wavelength for nanostructures coated with reagent on an illuminated substrate both before and after the reagent has reacted with a sample in accordance with an embodiment.

Consider, as an example, the scenario of FIG. 11, which is a graph in which the intensity I of light scattered from illuminated nano structures 52 has been plotted as a function of wavelength. As shown in FIG. 11, a test patch formed from nanostructures 52 coated with reagent 60 (or uncoated nanostructures 52) may initially exhibit a spectrum of the type shown by plasmonic spectrum 70 in FIG. 11 when illuminating by light from the light source in accessory 30. Spectrum 70 may be produced when the illumination from accessory 30 illuminates nanostructures 52 (e.g., nanorods) and causes nanostructures 52 to exhibit a plasmon resonance in which light is re-radiated outward from nanostructures 52 for detection by device 10. The reradiation pattern associated with the light scattered from nanostructures 52 may be affected by the shape of nanostructures 52. For example, in configurations in which nanostructures 52 are nanorods, nanostructure 52 may exhibit a dipole resonance behavior in which reradiated light experiences nulls aligned with the ends of the dipole. To help enhance the strength of the detected light spectrum at the rear-facing camera of device 10, it may be desirable to align the longitudinal axes of the nanorods parallel to the camera-facing surface of substrate 40 (and, in an illustrative configuration, perpendicular to the length of substrate 40 and optionally parallel to the electric field of illuminating light). In this configuration, illumination from the light source in accessory 30 may directed along the length of substrate 40 and may illuminate nanostructures 52 at a grazing angle of incidence. Because the nulls of the nanorods are oriented away from the rear-facing camera, signal strength is enhanced. Other nanostructure orientations may be used in patches 42 if desired.

In the example of FIG. 11, spectrum 70 (e.g., the spectrum of nanostructures 52 that are covered with reactant 60 but that have not reacted with a sample) peaks at a first wavelength $\lambda 1$ (e.g., a wavelength greater than 600 nm, another visible light wavelength, and/or an infrared and/or ultraviolet light wavelength). After exposure to a sample, a substance in the sample may bind to reagent coating 60, thereby forming coating 62 on nanostructures 52 and changing the optical properties of nanostructures 52, as described in connection with FIG. 10. This alters the plasmon resonance associated with nanostructures 52 and, in the example of FIG. 11, causes nanostructures 52 to exhibit altered spectrum 72 (e.g., a spectrum with a wavelength peak of $\lambda 2$, which is different than kl). By monitoring the light scattered from an illuminated set of test patches 42 on substrate 40, spectral changes can be measured and corresponding conclusions drawn about the presence or absence of substances of interest in the sample on the test patches.

Figure 12:
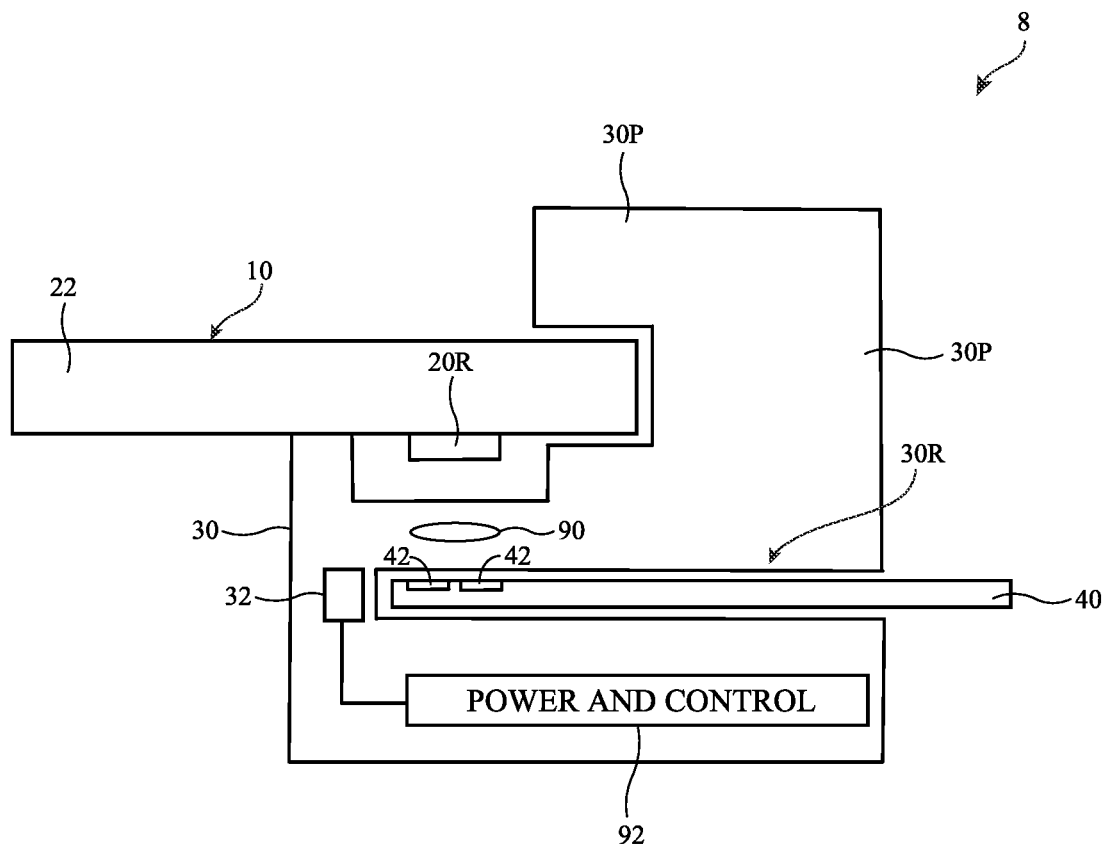
FIG. 12 is a cross-sectional side view of an illustrative system for testing samples in accordance with an embodiment.

An illustrative configuration for providing illumination to test patches 42 on substrate 40 is shown in FIG. 12. In the example of FIG. 12, device 10 of system 8 has front face F facing upwards and has rear face R facing downwards towards test substrate 40, so rear-facing camera 20R faces downwards. Accessory 30 has portions such as housing portions 30P that help couple accessory 30 to the upper edge of housing 22 of device 10. When coupled to device 10 in this way, accessory 30 is aligned with rear-facing camera 20R of device 10.

Accessory 30 (e.g., housing portion 30R) may be configured to form a recess or other structure to receive test substrate 40. Test substrate 40 may be, for example, a glass slide or other transparent planar member and portion 30R may be configured to form a slide-holding recess that receives the glass slide. Accessory 30 may have a lens such as lens 90 that is interposed between camera 20R and substrate 40. When received within accessory 30, test patches 42 on substrate 40 are aligned with rear-facing camera 40R and lens 90, so that camera 40R may capture images of test patches 42 and the material on test patches 42 (e.g., camera 40R may gather scattered light from test patches 42 to examine the surface of test patches 42 and to make measurements that reveal whether the spectrum of a patch has shifted due to binding between a sample and reactant 60, as described in connection with FIG. 11).

Accessory 30 may have power and control circuitry such as circuitry 92. Circuitry 92 may include a battery such as battery 34 of FIG. 3 or other source of power, control circuitry 16', input-output devices 12', etc. When it is desired to make a measurement on a sample on test patches 42, circuitry 92 (e.g., control circuitry 16') may turn on light source 32. Circuitry 92 may include a manually controlled switch (e.g., a switch that is manually controlled by a user of system 8) or may include an electrically adjustable switch that is controlled by a controller and used to control light source 32 (e.g., to turn light source 32 on or off). Control commands for turning light source 32 on and off may, if desired, be transmitted from device 10 to accessory 30 (e.g., wirelessly or via a wired connection). For example, a test application may be running on device 10. The test application may provide a user with a selectable on-screen option to commence a sample measurement. The on-screen option may be presented to the user on display 14 on front face F (as an example). In response to user selection of the on-screen option, device 10 may control accessory 30 so that accessory 30 turns on light source 32. In another illustrative configuration, light source 32 is turned on by a manual switch on accessory 30 or a switch that is activated by circuitry 92 when substrate sensor 31 detects that substrate 40 has been inserted into accessory 30. When light source 32 is turned on, battery power from accessory 30 or other source of power may be supplied to light source 32 so that light source 32 can illuminate test patches 42.

Light source 32 may contain solid state light-emitting devices such as light-emitting diodes and/or laser diodes (as examples). Laser diodes that may be used in light source 32 include vertical cavity surface-emitting lasers (VCSELS) and edge-emitting laser diodes. Configurations in which light source 32 include multiple light-emitting diodes may sometimes be described herein as an example. In general, however, any suitable light-emitting devices (e.g., semiconductor light-emitting devices such as laser diodes or light-emitting diodes) may be used in light source 32.

Figure 13:
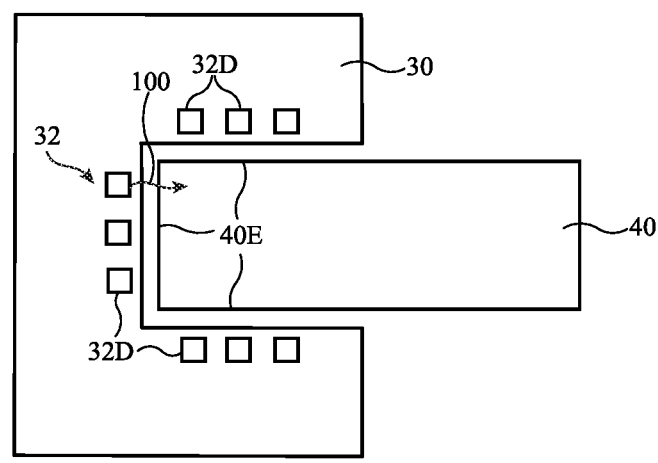
FIG. 13 is a top view of a portion of an accessory for providing edge illumination to a transparent substrate when testing samples in accordance with an embodiment.

The light-emitting diodes or other light-emitting devices of light source 32 may be arranged around the peripheral edge of substrate 40 so that light may be emitted into edges of substrate 40. FIG. 13 is a top view of accessory 30 and substrate 40 in an illustrative configuration in which light-emitting diodes 32D of light source 32 have been arranged in three sets each associated with a different one of three respective peripheral edges 40E of substrate 40 (which has four peripheral edge). If desired, light source 32 may include more light-emitting diodes 32D, one or more of the sets of light-emitting diodes 32D of FIG. 13 may be omitted, and/or other edge illumination systems may be used.

During operation, each light-emitting diode 32D (or laser or other light-emitting device) may emit light 100 into an adjacent edge surface of substrate 40 to illuminate samples on substrate 40. To enhance measurement sensitivity (e.g., to help enhance the accuracy with which system 8 can measure spectral shifts of the type described in connection with FIG. 11), one or more of light-emitting diodes 32D may be configured to emit light at a first wavelength (e.g., $\lambda 1$ of FIG. 11) and one or more of light-emitting diodes 32D may be configured to emit light at a second wavelength (e.g., $\lambda 2$ of FIG. 11) that is different than the first wavelength. If desired, diodes 32D may optionally emit light at one or more other probe wavelengths. The linewidth of diodes 32D may be less than 20 nm, less than 10 nm, less than 5 nm, less than 2 nm, less than 1 nm, at least 0.01 nm, or other suitable value.

Figure 14:
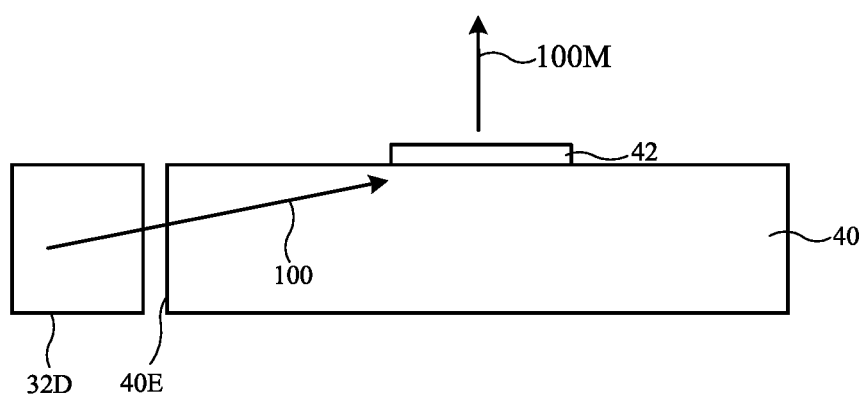
FIG. 14 is a cross-sectional side view of an illustrative transparent substrate with a test sample being illuminated in accordance with an embodiment.

A cross-sectional side view of accessory 30 and substrate 40 are shown in FIG. 14. As shown in FIG. 14, substrate 40 may have edges 40E that receive emitted light 100 from light-emitting diodes 32. Light 100 travels within the interior of substrate 40 (e.g., in a horizontal direction that is parallel or nearly parallel with upper planar surface 40P of substrate 40 (e.g., within less than 5°, less than 2°, or other suitable angle). As light 100 is traveling within substrate 40, the evanescent field associated with light 100 interacts with the sample. The evanescent field interactions of light 100 with nanostructures 52 causes some of light 100 to be extracted (out-coupled) from substrate 40P as light 100M. In this way, evanescent field coupling between light 100 and nanostructures 52 causes some of light 100 to be extracted as light 100M and to propagate away from the surface of substrate 40. Light that is extracted outwardly (scattered) from test patches 42 such as light 100M is extracted and caused to propagate in a direction that is perpendicular to the incoming illumination of light 100 (e.g., light 100 travels horizontally and scattered light 100M (e.g., light that has been out-coupled through evanescent field interactions with nanostructures 52) travels vertically towards rear-facing camera 20R).

This arrangement helps to enhance the signal-to-noise ratio of the spectral measurements being made (e.g., by helping to prevent any rays of light 100 from traveling directly between light-emitting diode 32D and rear-facing camera 20R without scattering from the nanostructures in test patches 42). Surface features are visible in the digital images captured with camera 20R to allow surface inspection, sample particle counting (e.g., particles of sample that have reacted with reactant 60), and/or other surface-feature analysis to be performed in addition to or instead of performing spectral analyses by, for example, comparing the intensity of measured light at wavelengths λ1 and λ2 to detect spectral shifts due to reaction of the sample with reactant 60.

System 8 may use personally identifiable information. It is well understood that the use of personally identifiable information should follow privacy policies and practices that are generally recognized as meeting or exceeding industry or governmental requirements for maintaining the privacy of users. In particular, personally identifiable information data should be managed and handled so as to minimize risks of unintentional or unauthorized access or use, and the nature of authorized use should be clearly indicated to users.

The foregoing is merely illustrative and various modifications can be made to the described embodiments. The foregoing embodiments may be implemented individually or in any combination.

| TABLE of Reference Numerals | | | |
|---|---|---|---|
| 10 | Electronic Device | 11 | Attachment mechanism |
| 30 | Accessory | 31 | Substrate sensor |
| 40 | Substrate | 8 | System |
| 16 | Control circuitry | 12 | Input-output devices |
| 14 | Display | 18 | Sensors |
| 20 | Cameras | 16' | Control circuitry |
| 12' | Input-output devices | 32 | Light source |
| 34 | Battery | 24 | Region |
| 22 | Housing | 26 | Region |
| F | Front face | R | Rear face |
| 42 | Patches | 52 | Nanostructures |
| 50 | Layer | 54 | Ridges |
| 56 | Grooves | 60 | Reactant |
| 62 | Sample substance | 70 | Spectrum |
| 72 | Spectrum | 30P, 30R | Portions |
| 20R | Rear-facing camera | 90 | Lens |
| 92 | Power and control circuitry | 40E | Edges |
| 100, 100M | Light | 32D | Light-emitting diodes |

What is claimed is:

1. An accessory that is operable with a portable electronic device to measure a sample on a transparent substrate that has nanostructures coated with reagent, wherein the portable electronic device comprises a camera, the accessory comprising:
a housing configured to removably couple to the portable electronic device and configured to receive the transparent substrate;
a lens supported by the housing in alignment with the camera; and
a light source configured to provide light to an edge of the transparent substrate to illuminate the nanostructures and cause the light to be extracted from the transparent substrate through evanescent field coupling with the nanostructures and to propagate away from a surface of the transparent substrate through the nanostructures and the lens to the camera, wherein the light source comprises a semiconductor light-emitting device, wherein the nanostructures comprise nanorods with aligned longitudinal axes, and wherein the illumination from the light source travels through the transparent substrate in a direction perpendicular to the aligned longitudinal axes.

2. The accessory defined in claim 1 wherein the light source comprises a first light-emitting device that emits light at a first wavelength and a second light-emitting device that emits light at a second wavelength.

3. The accessory defined in claim 1 wherein the light source comprises a first light-emitting device that emits light at a first wavelength and a second light-emitting device that emits light at a second wavelength, wherein the nanostructures are configured to exhibit a first plasmon resonance peak at the first wavelength when the reagent on the nanostructures has not reacted with the sample, and wherein the nanostructures are configured to exhibit a second plasmon resonance peak at the second wavelength when the reagent on the nanostructures has reacted with the sample.

4. The accessory defined in claim 1 wherein the nanostructures comprise metal nanostructures and wherein the reagent comprises an antibody.

5. The accessory defined in claim 4 wherein the semiconductor light-emitting device is one of first and second semiconductor light-emitting devices, wherein the first semiconductor light-emitting device is configured to emit light at a first wavelength and the second semiconductor light-emitting device is configured to emit light at a second wavelength that is different than the first wavelength.

6. The accessory defined in claim 5 wherein the first and second semiconductor light-emitting devices have linewidths of less than 5 nm.

7. The accessory defined in claim 1 further comprising a battery configured to power the light source.

8. The accessory defined in claim 1 further comprising a sensor configured to detect whether the transparent substrate is present within the accessory.

9. The accessory defined in claim 1 further comprising a magnet configured to attract the portable electronic device.

10. The accessory defined in claim 1 wherein the nanorods comprise metal nanorods, wherein the semiconductor light-emitting device is one of first and second semiconductor light-emitting devices, wherein the first semiconductor light-emitting device is configured to emit light coinciding with a spectral peak in a plasmon resonance of the metal nanorods exhibited when the sample has not reacted with the reagent, and wherein the second semiconductor light-emitting device is configured to emit light coinciding with a spectral peak in a plasmon resonance of the metal nanorods exhibited when the sample has reacted with the reagent.

11. An accessory configured to operate with an electronic device, comprising:
a housing configured to removably couple to the electronic device, wherein the housing has a portion configured to receive a transparent substrate that supports nanostructures and that has a first and second perpendicular edge surfaces, wherein at least some of the nanostructures are coated with reagent; and
light sources configured to emit light into the first and second perpendicular edge surfaces of the transparent substrate to illuminate the nanostructures and scatter light from the nanostructures in a perpendicular direction relative to the emitted light towards a sensor in the electronic device.

12. The accessory defined in claim 11 wherein the light sources comprise semiconductor light-emitting devices.

13. The accessory defined in claim 12 wherein the transparent substrate has four sides and wherein the semiconductor light-emitting devices are configured to emit light into at least three of the four sides.

14. The accessory defined in claim 11 wherein the nanostructures comprise metal nanoparticles with dimensions of less than 400 nm and wherein the light sources comprise at least one light-emitting device configured to emit light that has a linewidth of less than 5 nm and a wavelength of at least 600 nm.

15. A system for measuring biological samples, comprising:
   a cellular telephone with a rear-facing camera;
   a transparent substrate having nanostructures coated with reagent; and
   an accessory, comprising:
      a housing configured to receive the transparent substrate;
      a lens in the housing; and
      a light source in the housing that is configured to emit light into a peripheral edge of the transparent substrate to cause the light to scatter from the nanostructures through the lens into the rear-facing camera in a perpendicular direction relative to the emitted light, wherein the nanostructures comprise nanorods having nulls that are oriented away from the rear-facing camera.

16. The system defined in claim 15 wherein the nanorods comprise gold nanorods and wherein the reagent comprises an antibody.

17. The system defined in claim 16 wherein the light source comprises semiconductor light-emitting devices.

18. The system defined in claim 17 wherein the semiconductor light-emitting devices include a first semiconductor light-emitting device configured to emit light at a first wavelength and a second semiconductor light-emitting device configured to emit light at a second wavelength that is different than the first wavelength, and wherein the rear-facing camera is configured to measure the scattered light to detect spectral shifts in plasmon resonances of the nanostructures.

* * * * *